US006077280A

United States Patent [19]

Fossum

[11] Patent Number: 6,077,280
[45] **Date of Patent: *Jun. 20, 2000**

[54] SURGICAL CLAMP

[75] Inventor: Gregory T. Fossum, Gladwyne, Pa.

[73] Assignee: Thomas Jefferson University, Philadelphia, Pa.

[ * ] Notice: Under 35 U.S.C. 154(b), the term of this patent shall be extended for 374 days.

[21] Appl. No.: 08/496,604

[22] Filed: Jun. 29, 1995

[51] Int. Cl.[7] .................. A61B 17/08
[52] U.S. Cl. .................. 606/151; 606/205
[58] Field of Search .................. 606/151, 205, 606/206, 207, 208; 81/300; 128/751

[56] References Cited

U.S. PATENT DOCUMENTS

| | | | |
|---|---|---|---|
| D. 246,190 | 10/1977 | Hodge | D24/27 |
| 2,618,268 | 11/1952 | English | 128/321 |
| 2,668,538 | 2/1954 | Baker | 128/321 |
| 2,842,132 | 7/1958 | Soltero et al. | 128/322 |
| 3,913,586 | 10/1975 | Baumgarten | 128/325 |
| 3,981,308 | 9/1976 | Schlein | 606/205 |
| 4,574,804 | 3/1986 | Kurwa | 606/207 |
| 5,059,214 | 10/1991 | Akopov et al. | 606/207 |

OTHER PUBLICATIONS

Vrazo, F., "Difficulties Surfacing for Norplant", The Philadelphia Inquirer Jul. 7, 1994.

*Primary Examiner*—Michael Buiz
*Assistant Examiner*—Daphna Shai
*Attorney, Agent, or Firm*—Woodcock Washburn Kurtz Mackiewicz & Norris LLP

[57] ABSTRACT

The present invention provides a new surgical clamp which provides for sufficient gripping of a foreign body and for the safe removal of a foreign body. A surgical clamp is provided having a pair of intersecting arms and a pivot interconnecting the arms for providing rotating motion about the pivot. The arms each comprise a handle portion, a jaw portion, and a shaft portion between the handle and jaw portions. The handle portion further comprises a finger loop and a latching mechanism opposite the finger loop. The jaw portion is preferably tapered, curved, and has a rat tooth at the distal end. The jaw portion also preferably has a gripping surface comprising a diamond grid pattern. The gripping surfaces on each jaw is operably opposed and the latching mechanism operably engageable when the handle portions are rotated toward each other for holding the handle portions in a fixed position, and operably engaging the gripping surfaces.

9 Claims, 5 Drawing Sheets

SURGICAL CLAMP

FIELD OF THE INVENTION

The present invention relates to surgical clamps useful for removing foreign bodies during surgical procedures.

BACKGROUND OF THE INVENTION

Goals of surgical procedures include, inter alia, making the smallest incision possible and ensuring that the procedure is performed optimally such that any further corrective procedures are not warranted, or are at least kept to a minimum. Surgical clamps are very critical instruments which play an important role during many surgical procedures. Existing surgical clamps include those used to remove foreign bodies, such as, for example, glass, metal, and NORPLANT™ contraceptive capsules. Presently these types of foreign bodies are removed by making an incision and grasping the foreign object with a curved-jaw, locking clamp known as a "mosquito clamp". However, the clamps available on the market are inadequate in that they do not sufficiently grasp the foreign object, and are also of a size that requires an excessively large incision.

U.S. Pat. No. 2,618,268 describes a surgical clamp with curved crossed members which provide accessibility. This clamp also comprises a rat-tooth like structure and longitudinal grooves on the crossed members.

U.S. Pat. No. 2,668,538 describes a surgical clamp with serrations on the crossed members.

U.S. Pat. No. 2,842,132 describes a surgical clamp with a tooth and recess for the tooth at the tip of the jaws.

U.S. Pat. No. 3,913,586 describes a hemostat with the general structure of a typical clamp.

U.S. Pat. No. 5,059,214 describes a surgical forceps with a projection and a recess on the tip of the jaws. The jaws may also be curved as well as tapered.

U.S. Pat. No. D246,190 depicts a hepatic occlusion clamp.

None of the surgical clamps or hemostats currently available are optimal for removing foreign bodies, such as, for example, NORPLANT™ contraceptive capsules. The clamps are either too large or do not sufficiently grasp the foreign body. In addition, some of the clamps have a pattern of transverse grooves which does not provide for adequate gripping. As a result of using the currently available clamps, a larger incision is required. In addition, the foreign body sometimes slips from the clamp jaws, necessitating further surgical procedures to remove the foreign body. If the foreign body is a capsule containing a medicament, such as a NORPLANT™ capsule or any other capsule containing a medicament, such slipping can cause unwanted damage to the capsule or even necessitate further surgical removal procedures.

The present invention provides a solution to a longstanding problem of inadequate surgical clamps. The present invention provides a new surgical clamp which provides for sufficient gripping of a foreign body and for the safe removal of a foreign body. The present invention also allows for a smaller incision during surgery.

SUMMARY OF THE INVENTION

The present invention is related to a surgical clamp comprising a pair of intersecting arms and pivot means interconnecting the arms for providing rotating motion about a common axis, each arm comprising handle portion, jaw portion, and shaft portion between the handle and jaw portions, each handle portion further comprising finger loop and latching means opposite the finger loop and in substantially the same plane therewith, each jaw portion further comprising diamond grid gripping surface, and the gripping surface on each jaw being operably opposed and the latching means being operably engageable when the handle portions are rotated toward each other for holding the handle portions in a fixed position, and operably engaging the gripping surfaces.

The present invention is also related to a surgical clamp comprising a pair of intersecting arms and pivot means interconnecting the arms for providing rotating motion about a common axis, each arm comprising handle portion, jaw portion, and shaft portion between the handle and jaw portions, the handle portion further comprising finger loop and latching means opposite the finger loop and in substantially the same plane therewith, the jaw portion being tapered and curved in a plane perpendicular to the arms, the jaw portion further comprising a single pointed rat tooth at the distal end and a diamond grid gripping surface, and the gripping surfaces on each jaw being operably opposed and the latching means being operably engageable when the handle portions are rotated toward each other for holding the handle portions in a fixed position, and operably engaging the gripping surfaces.

BRIEF DESCRIPTION OF THE FIGURES

FIG. 2A shows a single point rat tooth. FIG. 2B shows a double point rat tooth. FIG. 2C shows a squarish rat tooth. FIG. 2D shows a curved rat tooth.

DETAILED DESCRIPTION OF THE INVENTION

Figure 1A:
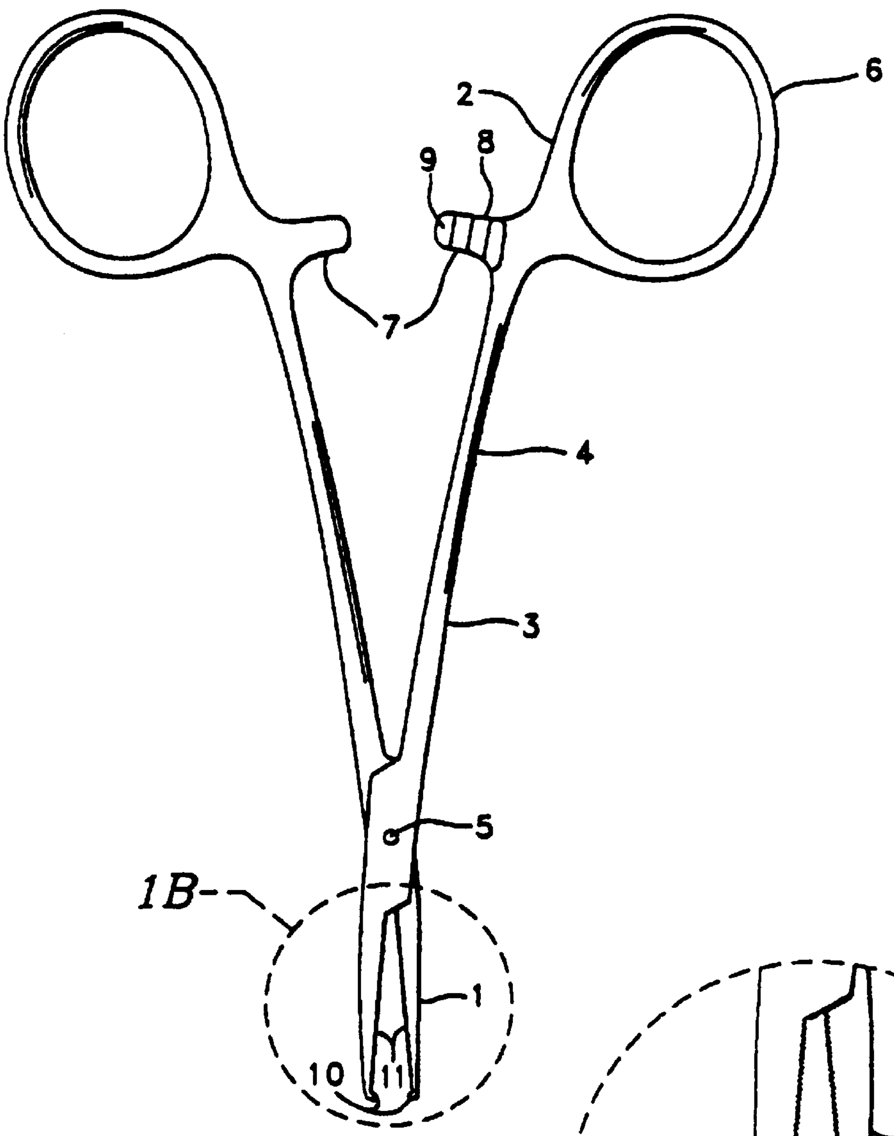
FIG. 1A depicts a top view of a surgical clamp of the present invention.

According to the present invention, surgical clamps are provided having a gripping surface sufficient to remove foreign bodies. The surgical clamps comprise a pair of intersecting arms and pivot means interconnecting the arms for providing rotating motion about a common axis. The arms each comprise a handle portion, a jaw portion, and a shaft portion between the handle and jaw portions. The handle portion further comprises a finger loop and a latching means opposite the finger loop and in substantially the same plane therewith. The jaw portion further comprises a diamond grid gripping surface. The gripping surface on each jaw is operably opposed and the latching means is operably engageable when the handle portions are rotated toward each other for holding the handle portions in a fixed position, and operably engaging the gripping surfaces.

As used herein, the term "rat tooth" is meant to refer to the terminal portion of a pair of interacting jaw portions of a clamp, wherein a first jaw portion comprises a gripping portion having a gripping tooth and a second jaw portion comprises a receiving portion having a corresponding receiving groove for receiving and meshing with the gripping tooth of the first jaw portion.

Briefly stated, methods for making one arm of an intersecting pair of arms comprises forming a metal core having a handle portion, a jaw portion and a shaft portion intermediate the handle portion and the jaw portion. Materials for making the surgical clamp include, for example, stainless steel, tempered steel, polymer plastics, and the like. Any such material sufficient for surgical use may be used to manufacture the present invention. The metal core may be tempered, or may be encased in plastic by, for example, injection molding or insert molding. The polymer used to mold the clamp can be any available extrudable polymers, such as, for example, polypropylene, polybutene, polyamides, polyamines, polymethacrylates and polymethylmethacrylates, and the like. A desirable characteristic for any polymeric material employed is resistance to high temperature deformation, which would provide for heat sterilization. Those skilled in the art of manufacturing surgical clamps will be readily able to manufacture the present invention by a variety of manufacturing techniques. One arm of the clamp is attached at the end of the shaft distal to the handle portion with another similarly formed arm to form a pair of intersecting arms. The attachment of the arms is provided by a pivot means interconnecting the arms for providing a swinging motion about a common axis.

Surgical clamps of the present invention are shown in FIGS. 1–5. FIG. 1A shows a top view of a typical surgical clamp of the present invention. Each arm 4 of the surgical clamp, although preferably one piece, consists of three decernable elements, the handle portion 2, the shaft portion 3 and the jaw portion 1. The jaw portion and the handle portion are shown to be in substantially the same plane with the shaft portion being intermediate therewith so that the two halves or arms of the clamp will aline and place the handle and jaw portions of each arm in about the same plane.

The two arms of the clamp are pivotally connected by a pivot means 5, wherein a pin or other pivot means is placed through the two arms joining them at the shaft. The pivot means may completely penetrate the arms of the clamp or may only partially penetrate the arms of the clamp.

The handle of each arm further comprises a finger loop 6, and latching means 7 opposite the finger loop and in substantially the same plane therewith. Alternatively, the finger loop may be in a plane that intersects the plane of the arm. The finger loop of the handle is generally of a size sufficient to accommodate human fingers. Latching means 7 is shown in the open position, hence providing that the jaws of the clamp are open. The latching means of each handle portion is attached on the interior surface of the handle portion. The latching means of each handle are directly opposed when the two arms of the clamp are pulled together at the handle portions such that the latching surface 8 of each latching means cause the two arms to interconnect with each other thereby engaging the latching teeth 9 and locking the clamp in a desired position. The teeth 9 are released by using the finger loops to distort the arms and temporarily disengaging the teeth and allowing the clamp to be opened.

Figure 1B:
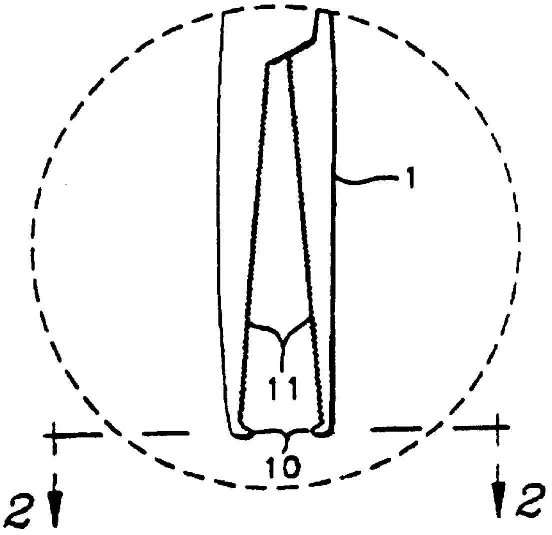
FIG. 1B shows an enlarged view of the jaw portion of the clamp depicted in FIG. 1A.

FIG. 1B shows an enlarged view of the jaw portions of each arm of a typical clamp of the present invention. The jaw portion of the clamps may be smooth or, as depicted in FIG. 1B, may further comprise a gripping surface 11 on the interior surface of the jaw. In a preferred embodiment, the two opposed jaw portions are tapered such that the distal end of the jaw is narrower than the portion of the jaw proximal to the shaft portion of the arm. Alterntively, the jaw portion may not be tapered. In a preferred embodiment, the terminal portion of the jaw portion of each arm of clamps of the present invention terminate to collectively provide a rat tooth 10, as depicted in FIG. 1B. Alternatively, the clamp of the present invention may have no rat tooth.

FIG. 2 shows cross-sectional views of several types of rat tooths of the present invention. The views correspond to the view of the distal tip of the jaw portion as indicated in FIG. 1B. The terminal portion of both jaw portions of the clamp collectively comprise a rat tooth 10, having a first half, the gripping portion 12, and a second half, the receiving portion 13. The gripping portion forms the terminal portion of one jaw portion of a clamp and the receiving portion forms the terminal portion of the other jaw portion of the clamp. The gripping tooth and the receiving groove form a tight grip on an object when the two arms of the clamp are juxtaposed such that the latching means is engaged.

Figure 2A:
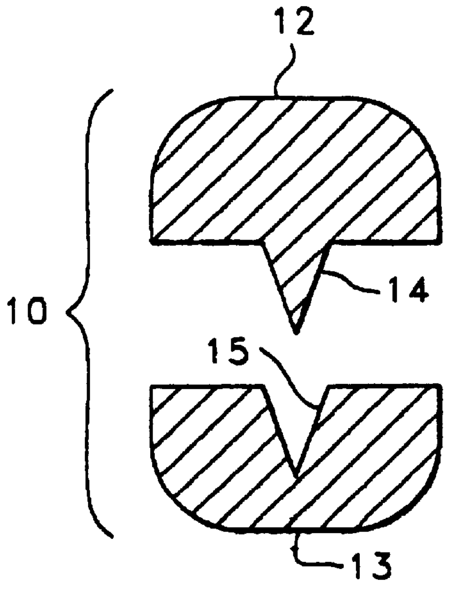
FIGS. 2A, 2B, 2C and 2D show cross-sectional views of several types of rat tooths that may comprise the terminal tip of the jaw portion of surgical clamps of the invention, such as those depicted in FIGS. 1A and 1B.

In one embodiment of the present invention, as shown in FIG. 2A, the gripping portion of the rat tooth comprises a single pointed gripping tooth 14, and the receiving portion comprises a corresponding single pointed receiving groove 15, to form a tight seal with the single pointed gripping tooth. Such a rat tooth is called a single pointed rat tooth.

Figure 2B:
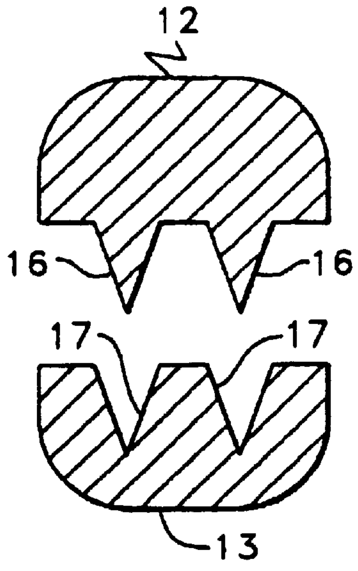

In another embodiment of the present invention, as shown in FIG. 2B, the gripping portion of the rat tooth comprises a double pointed gripping tooth 16, and the receiving portion comprises a corresponding double pointed receiving groove 17, to form a tight seal with the double pointed gripping tooth. Such a rat tooth is called a double pointed rat tooth.

Figure 2C:
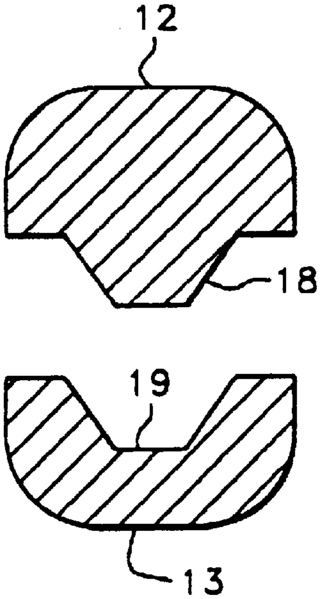

In another embodiment of the present invention, as shown in FIG. 2C, the gripping portion of the rat tooth comprises a squarish gripping tooth 18, and the receiving portion comprises a corresponding squarish receiving groove 19, to form a tight seal with the squarish gripping tooth. Such a rat tooth is called a squarish rat tooth.

Figure 2D:
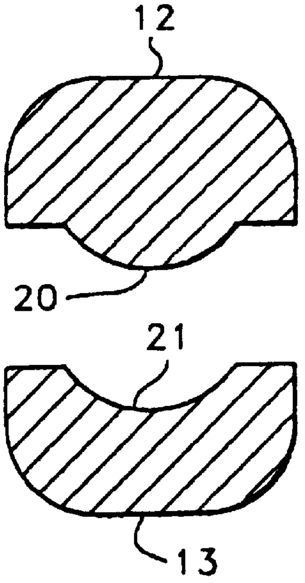

In another embodiment of the present invention, as shown in FIG. 2D, the gripping portion of the rat tooth comprises a curved gripping tooth 20, and the receiving portion comprises a corresponding curved receiving groove 21, to form a tight seal with the curved gripping tooth. Such a rat tooth is called a curved rat tooth. Rat tooths of the invention may alternatively comprise other configurations not depicted.

Figure 3A:
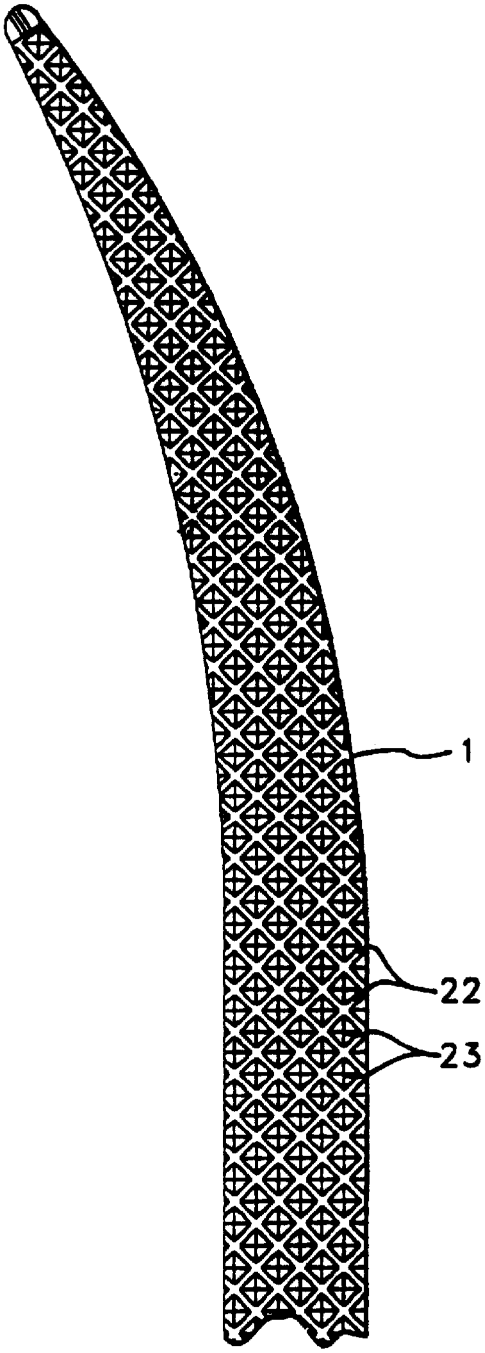
FIG. 3A shows a top view of gripping surface of a jaw portion of a surgical clamp wherein the gripping channels intersect each other at 90° angles.
Figure 3B:
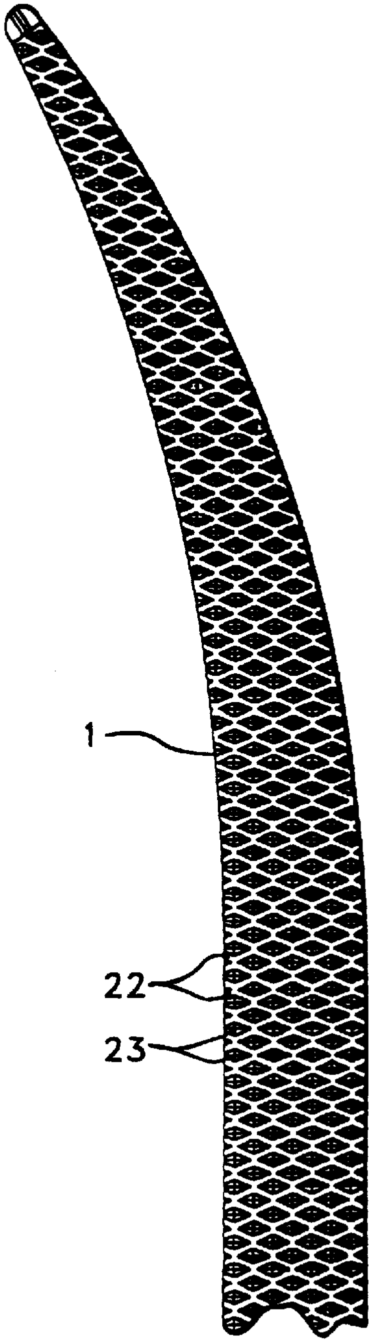
FIG. 3B shows a top view of gripping surface of a jaw portion of a surgical clamp wherein the gripping channels intersect each other at 45° angles.

FIGS. 3A and 3B depict gripping surfaces of a jaw portion of a clamp of the present invention. The gripping surface of the jaw portion of each arm of the clamp opposedly interact to grasp a foreign object. The gripping surface of the present invention is formed by providing intersecting channels 22 which form gripping peaks 23 therebetween. Such a gripping surface is called a diamond grid gripping surface. The intersecting channels are preferably provided such that they are not perpendicular to the side of the jaw portion of the clamp. The intersecting channels preferably intersect each other at 90° angles, as depicted in FIG. 3A. Thus, the intersecting channels form a grid pattern which provides diamond-shaped gripping peaks. Alternatively, the intersecting channels may intersect with each other at less than 90° angles, such as, for example, at 45° angles, as depicted in FIG. 3B, thus forming extended diamond-shaped gripping peaks. The gripping channels may intersect each other at angles ranging from 1° to 90°. Preferably, the gripping channels intersect forming 90° angles. The gripping peaks may be flat or raised to form pyramid-shaped peaks.

Figure 4:
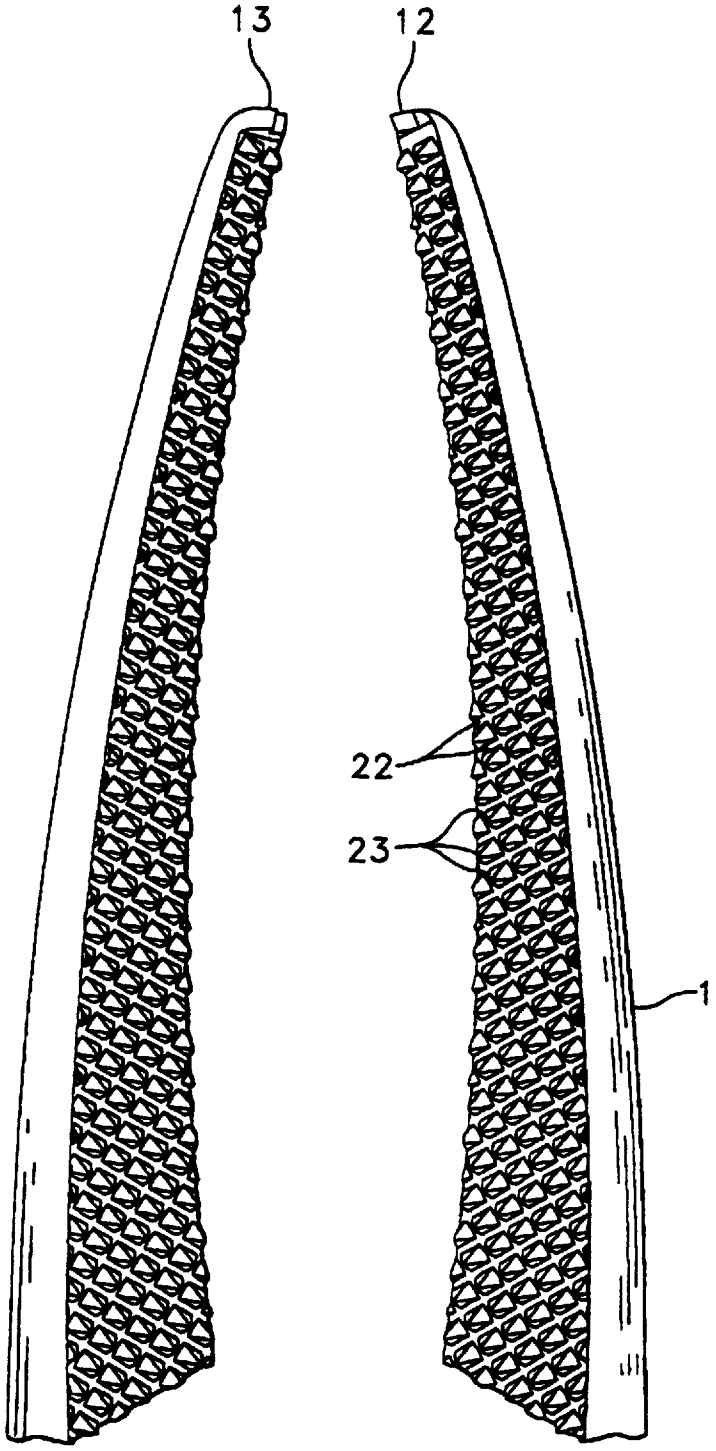
FIG. 4 shows a prospective view of jaw portions of a surgical clamp of the present invention.

A preferred embodiment of the present invention is depicted in FIG. 4, which depicts a prospective view of a pair of interacting jaw portions having a single pointed rat tooth and having a diamond grid gripping surface formed by intersecting channels, intersecting at 90°, wherein the gripping peaks are raised pyramids. The raised pyramid peaks may range from about 0.001 mm to 5 mm in height.

Figure 5:
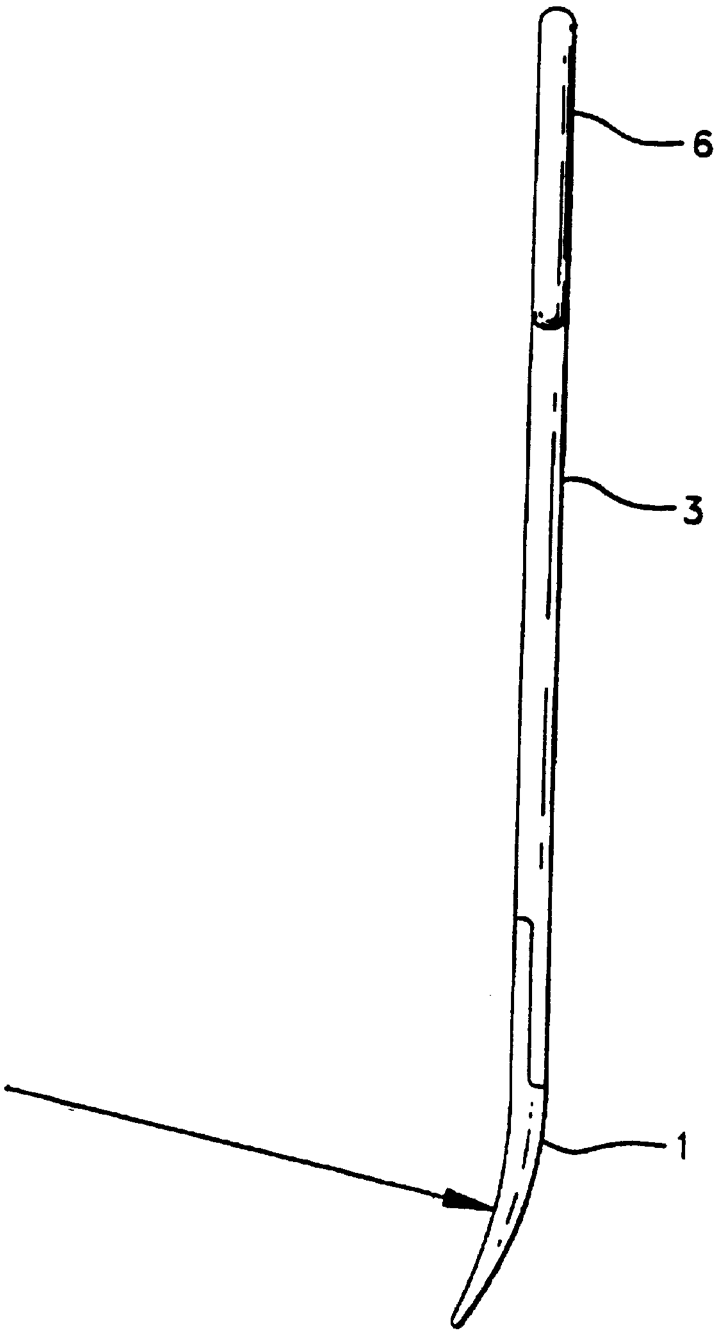
FIG. 5 shows a side view of a surgical clamp of the present invention, wherein the jaw portion has a radius of curvature r.

FIG. 5 shows a side view of a typical clamp of the present invention, wherein the jaw portion of the clamp is curved. In one embodiment of the invention, the jaw portion is curved in a plane perpendicular to the plane of the arms of the clamp, as depicted in FIG. 5. The curvature of the jaws is indicated as having a radius r having a linear distance of between about 0.5 and 12 inches. Preferably, the radius of curvature r is between about 1.0 and 5.0 inches.

In another embodiment of the present invention, the jaw portion of the clamp is curved in the same plane as the arms of the clamp. In another embodiment of the present invention, the jaw portion of the clamp is curved both in the same plane as the arms of the clamp and in a plane perpendicular to the plane of the arms of the clamp. The curvature of the jaws preferably has a radius r having a linear distance of between about 0.5 and 12 inches, and more preferably has a radius between about 1.0 and 5.0 inches.

A preferred clamp of the present invention comprises a pair of intersecting arms and pivot means interconnecting the arms for providing rotating motion about a common axis. Each of the arms comprise a handle portion, a jaw portion, and a shaft portion between the handle and jaw portions. Each handle portion further comprises a finger loop and a latching means opposite the finger loop and in substantially the same plane therewith. Each jaw portion further comprises a diamond grid gripping surface. The gripping surface is operably opposed and the latching means is operably engageable when the handle portions are rotated toward each other for holding the handle portions in a fixed position, and operably engaging the gripping surfaces.

In a preferred embodiment of the invention, the clamp described above further comprises a tapered jaw portion which is curved in a plane perpendicular to the arms, having a radius of curvature r of between about 1.0 and 5.0 inches. The jaw portion further comprises a single pointed rat tooth at the distal end and a diamond grid gripping surface formed by gripping channels intersecting at 90° angles and raised pyramid-like gripping peaks.

The present invention may be used to remove foreign bodies, such as, for example, glass, metal, and NORPLANT™ contraceptive capsules. In such procedures, a small incision is made in the skin of an individual in order to remove a foreign object, such as a NORPLANT™ contraceptive capsule. Alternatively, an existing incision, present as a result of trauma to the skin and/or underlying tissue, is used to remove a foreign object such as glass or metal. The present invention provides a new surgical clamp which provides for sufficient gripping of a foreign body and for the safe removal of a foreign body. The present invention, due to its tapering jaw portions also allows for a smaller incision during surgery.

Once the incision is made, the foreign object is grasped with the jaw portions of the clamp by rotating the handle portion of the arms of the clamps together. The object is firmly grasped within the diamond grid gripping pattern and the clamp is locked in position by the interaction of the latching teeth on opposite latching means of each handle portion of the clamp. The object is then removed from the skin or underlying tissue.

What is claimed is:

1. A surgical clamp comprising:

a pair of intersecting arms and pivot means interconnecting said arms for providing rotating motion about a common axis;

said arms each comprising handle portion, jaw portion, and shaft portion between said handle and jaw portions;

each handle portion further comprising finger loop and latching means opposite said finger loop and in substantially the same plane therewith;

each jaw portion is curved and comprises rat tooth at the distal end and diamond grid gripping surface; and said gripping surface on each jaw being operably opposed and said latching means being operably engageable when said handle portions are rotated toward each other for holding said handle portions in a fixed position, and operably engaging said gripping surfaces.

2. The clamp of claim 1, wherein the jaw portion is tapered.

3. The clamp of claim 2 having rat tooth selected from the group consisting of a single pointed rat tooth, double pointed rat tooth, squarish rat tooth, and curved rat tooth.

4. The clamp of claim 3 wherein said jaw portion has a radius of curvature between about 0.5 to 12.0 inches and a single pointed rat tooth.

5. The clamp of claim 3 wherein said jaw portion has a radius of curvature between about 0.5 to 5.0 inches and a single pointed rat tooth.

6. The clamp of claim 1 having rat tooth selected from the group consisting of a single pointed rat tooth, double pointed rat tooth, squarish rat tooth, and curved rat tooth.

7. The clamp of claim 6 wherein said jaw portion has a radius of curvature between about 0.5 to 12.0 inches and a single pointed rat tooth.

8. The clamp of claim 6 wherein said jaw portion has a radius of curvature between about 0.5 to 5.0 inches and a single pointed rat tooth.

9. A surgical clamp comprising:

a pair of intersecting arms and pivot means interconnecting said arms for providing rotating motion about a common axis;

said arms each comprising handle portion, jaw portion, and shaft portion between said handle and jaw portions;

said handle portion further comprising finger loop and latching means opposite said finger loop and in substantially the same plane therewith;

said jaw portion being tapered and curved in a plane perpendicular to said arms;

said jaw portion further comprising a single pointed rat tooth at the distal end and a diamond grid gripping surface; and said gripping surfaces on each jaw being operably opposed and said latching means being operably engageable when said handle portions are rotated toward each other for holding said handle portions in a fixed position, and operably engaging said gripping surfaces.

* * * * *